United States Patent [19]

Hawkins et al.

[11] Patent Number: 4,473,395

[45] Date of Patent: Sep. 25, 1984

[54] METHOD FOR INDUCING TILLERING UTILIZING CERTAIN PYRIDINE-1-OXIDES

[75] Inventors: Alan F. Hawkins; David P. J. Pearson, both of Woodley; Gilbert J. Stacey, Peel Hall, all of England

[73] Assignee: Imperial Chemical Industries PLC, London, England

[21] Appl. No.: 379,047

[22] Filed: May 17, 1982

[30] Foreign Application Priority Data

May 19, 1981 [GB] United Kingdom ............... 8115251
May 19, 1981 [GB] United Kingdom ............... 8115252
Aug. 14, 1981 [GB] United Kingdom ............... 8124941

[51] Int. Cl.$^3$ ............... C07D 213/55; A01N 43/40
[52] U.S. Cl. ........................... 71/94; 546/5; 546/322

[58] Field of Search ............... 71/94; 546/322, 5

[56] References Cited

FOREIGN PATENT DOCUMENTS 6359  9/1980  European Pat. Off. ............ 546/303
2395996  1/1979  France ............................. 546/298

Primary Examiner—Alan L. Rotman
Attorney, Agent, or Firm—Cushman, Darby & Cushman

[57] ABSTRACT

This invention relates to a method of inducing tillering in cereal plants using certain 5-phenyl-3-pyridinecarboxylate compounds, to certain of the compounds themselves, to a process for preparing these compounds, and to agricultural compositions containing them. The compounds are also useful as intermediates for preparing other of the compounds.

9 Claims, No Drawings

METHOD FOR INDUCING TILLERING UTILIZING CERTAIN PYRIDINE-1-OXIDES

BACKGROUND OF THE INVENTION

The invention provides a method of inducing tiller formation in a monocotyledonous plant, the method comprising applying to the plant, to seed of the plant or to the locus surrounding the plant or seed, a compound of general formula (I):

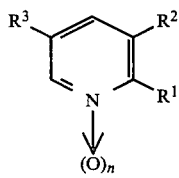

wherein $R^1$ is hydrogen, halogen, optionally halo- or acetoxy-substituted $C_{1-4}$ alkyl (for example methyl, dichloromethyl, trifluoromethyl or acetoxymethyl), hydroxy, amino, phenyl or ($C_{1-5}$ alkoxy) carbonyl; $R^2$ is cyano, or a group of general formula $-COR^4$ wherein $R^4$ is $-O^-1/m\ M^{m+}$, $-OR^5$, $-SR^6$, $-NR^7R^8$ or $-NR^9-NR^{10}R^{11}$ wherein M is an m-valent cation e.g. an alkali metal, alkaline earth metal, copper or iron ion or a mono-, di-, tri- or tetra ($C_{1-6}$ alkyl) substituted or unsubstituted ammonium ion;

$R^5$ is $C_{1-8}$ alkyl (e.g. $C_{1-5}$ alkyl) optionally substituted with halogen, hydroxy, cyano, $C_{1-4}$ alkoxy, $C_{1-4}$ alkylthio, carboxy, ($C_{1-4}$ alkoxy)carbonyl, $C_{3-6}$ cycloalkyl, amino, mono- or di- $C_{1-4}$ alkylamino, a 5- or 6-membered heterocyclic ring or optionally halo- or $C_{1-4}$ alkyl-substituted phenyl; $C_{3-6}$ cycloalkyl; optionally halo-substituted $C_{2-6}$ alkenyl (e.g. $C_{3-5}$ alkenyl); $C_{3-6}$ alkynyl; or phenyl optionally substituted with halogen, $C_{1-4}$ alkyl, $C_{1-4}$ alkoxy, $C_{1-4}$ alkylthio, cyano or nitro;

$R^6$ is $C_{1-8}$ alkyl optionally substituted with $C_{3-6}$ cycloalkyl, ($C_{1-4}$ alkoxy)carbonyl, halogen, cyano, a 5- or 6-membered heterocyclic ring or optionally halo- or $C_{1-4}$ alkyl-substituted phenyl; $C_{3-6}$ cycloalkyl; $C_{3-6}$ alkenyl; or phenyl optionally substituted with halogen, $C_{1-4}$ alkyl, $C_{1-4}$ alkoxy, $C_{1-4}$ alkylthio, cyano or nitro;

each of $R^7$ and $R^8$, which may be the same or different, is hydrogen; $C_{1-6}$ alkyl (e.g. $C_{1-4}$ alkyl) optionally substituted with hydroxy, halogen, cyano, ($C_{1-4}$ alkoxy)carbonyl, $C_{1-4}$ alkoxy or $C_{3-6}$ cycloalkyl; $C_{1-4}$ alkoxy; $C_{3-6}$ alkenyl; $C_{3-6}$ alkynyl; $C_{3-6}$ cycloalkyl; ($C_{1-6}$ alkane)-sulphonyl (for example methane sulphonyl); hydroxy; or phenyl or benzyl optionally ring-substituted by halogen, $C_{1-4}$ alkyl, $C_{1-4}$ alkoxy, $C_{1-4}$ alkylthio, ($C_{1-4}$ alkoxy)-carbonyl, cyano or nitro; or $R^7$ or $R^8$ together with the nitrogen atom to which they are bound form a 5- or 6-membered heterocyclic ring optionally containing a further hetero atom;

$R^9$ is hydrogen, $C_{1-4}$ alkyl, phenyl or benzyl;

each of $R^{10}$ and $R^{11}$, which may be the same or different, is hydrogen; $C_{1-4}$ alkyl; ($C_{1-4}$ alkoxy) ($C_{1-4}$ alkyl); $C_{2-6}$ alkanoyl; or benzoyl or phenyl optionally substituted with halogen, $C_{1-4}$ alkyl or $C_{1-4}$ alkoxy, or $R^{10}$ and $R^{11}$ together with the nitrogen atom to which they are bound for a 5- or 6-membered heterocyclic ring optionally containing a further hetero atom;

$R^3$ is optionally halo-, haloalkyl- (e.g. trifluoromethyl-), haloalkoxy- (e.g. trifluoromethoxy), nitro-, cyano-, hydroxy-, amino-, acylamino- (e.g. acetamido-), mono- or di-alkylamino-, $C_{1-4}$ alkyl-, $C_{1-4}$ alkoxy, $C_{1-4}$ alkylthio-, $C_{1-4}$ alkylsulphinyl-, $C_{1-4}$ alkylsulphonyl-, $C_{2-6}$ alkenyl-, carboxy-, $C_{1-4}$ alkoxycarbonyl- or carboxamido-substituted phenyl; and n is 0 or 1;

or, when n is 0, an acid addition salt thereof.

The alkyl and alkoxy groups in the above definitions are suitably methyl, ethyl, propyl (n- or i-propyl), butyl (n-, i-, sec- or t-butyl), methoxy or ethoxy. Suitable cycloalkyl, alkenyl and alkynyl groups are cyclohexyl, allyl and propargyl, respectively. A suitable alkali or alkaline earth metal is sodium, potassium or calcium. The halogen is suitably fluorine, chlorine, bromine or iodine.

Suitable $R^3$ groups are phenyl itself, o-, m- or p-fluoro-, chloro-, bromo-, cyano-, acetylamino-, amino-, nitro-, methyl-, trifluoromethyl- or methoxy-phenyl, dihalophenyl for example dichlorophenyl (e.g. 2,4-dichlorophenyl) and dibromophenyl (e.g. 3,5-dibromophenyl), 3-bromo-4-aminophenyl and 3,5-dibromo-4-aminophenyl. Preferred $R^2$ group is alkoxycarbonyl particularly ethoxy- and n-propoxy-carbonyl.

Examples of suitable compounds of general formula (I) are shown in Table 1.

TABLE 1

| COMPOUND NUMBER | $R^1$ | $R^2$ | $R^3$ | n | Melting Point (°C.) |
|---|---|---|---|---|---|
| 1 | Me | COOEt | p-Cl—$C_6H_4$— | 0 | 71 |
| 2 | Me | COOEt | p-Br—$C_6H_4$— | 0 | 86 |
| 3 | Me | COOEt | p-NO—$C^2_6H_4$— | 0 | 120 |
| 4 | Me | COOEt | $C_6H_5$— | 0 | 48 |
| 5 | Me | COOEt | p-Me—$C_6H_4$— | 0 | 43 |
| 6 | Me | COOEt | p-F—$C_6H_4$— | 0 | 74 |
| 7 | Me | COOEt | p-MeO—$C_6H_4$— | 0 | 41 |
| 8 | Me | COOEt | o-Cl—$C_6H_4$— | 0 | 79 |
| 9 | Me | COOEt | 2,4-diCl—$C_6H_3$— | 0 | |
| 10 | Me | COOEt | p-Cl—$C_6H_4$— | 0 | 297–300 (dec*) |
| 11 | Me | CONH$_2$ | p-Cl—$C_6H_4$— | 0 | 209 (dec) |
| 12 | Me | CONHSO$_2$Me | p-Cl—$C_6H_4$— | 0 | 209–11 |
| 13 | Me | COO—n-Bu | p-Cl—$C_6H_4$— | 0 | 56 |
| 14 | Me | CN | p-Cl—$C_6H_4$— | 0 | 158–9 |
| 15 | Me | COOMe | p-Cl—$C_6H_4$— | 0 | 107–9 |
| 16 | Me | COO—n-Pr | p-Cl—$C_6H_4$— | 0 | 54–7 |
| 17 | Me | COO—t-Bu | p-Cl—$C_6H_4$— | 0 | 70–72 |
| 18 | Me | COOCH$_2$CH=CH$_2$ | p-Cl—$C_6H_4$— | 0 | |
| 19 | Me | COO(CH$_2$)$_2$OH | p-Cl—$C_6H_4$— | 0 | 93–95 |
| 20 | Me | COOCH$_2$C$_6$H$_5$ | p-Cl—$C_6H_4$— | 0 | 83–85 |

TABLE 1-continued

| COMPOUND NUMBER | R$^1$ | R$^2$ | R$^3$ | n | Melting Point (°C.) |
|---|---|---|---|---|---|
| 21 | Me | COO—⬡ | p-Cl—C$_6$H$_4$— | 0 | 67–69 |
| 22 | Me | CONMe$_2$ | p-Cl—C$_6$H$_4$— | 0 | 133–136 |
| 23 | Me | CONHCH$_2$CH=CH$_2$ | p-Cl—C$_6$H$_4$— | 0 | 131–133 |
| 24 | Me | CONHC$_6$H$_5$ | p-Cl—C$_6$H$_4$— | 0 | 79–82 |
| 25 | Me | CONHCH$_2$C$_6$H$_5$ | p-Cl—C$_6$H$_4$— | 0 | 163–165 |
| 26 | Me | CONHOH | p-Cl—C$_6$H$_4$— | 0 | 186–187 |
| 27 | Me | CONHNH$_2$ | p-Cl—C$_6$H$_4$— | 0 | 184–186 |
| 28 | Me | CONHNMe$_2$ | p-Cl—C$_6$H$_4$— | 0 | |
| 29 | Me | COO—i-Bu | p-Cl—C$_6$H$_4$— | 0 | |
| 30 | Me | COOEt | p-CF$_3$—C$_6$H$_4$— | 0 | 86–87 |
| 31 | Me | COOEt | m-CF$_3$—C$_6$H$_4$— | 0 | 82–83 |
| 32 | Me | COOEt | m-Br—C$_6$H$_4$— | 0 | 90–91 |
| 33 | Me | COOEt | 3,5-diBr—C$_6$H$_3$— | 0 | 100–102 |
| 34 | Me | COOEt | p-NH$_2$—C$_6$H$_4$— | 0 | 137–138 |
| 35 | Me | COOEt | p-CH$_3$CONH—C$_6$H$_4$ | 0 | 148–150 |
| 36 | Me | COOEt | 3-Br—4-NH$_2$—C$_6$H$_4$— | 0 | 126–128 |
| 37 | Me | COOEt | 3,5-diBr—4-NH$_2$—C$_6$H$_2$— | 0 | 171 (dec) |
| 38 | Cl | CN | C$_6$H$_5$— | 0 | |
| 39 | H | CN | C$_6$H$_5$— | 0 | |
| 40 | H | COOH | C$_6$H$_5$— | 0 | |
| 41 | H | COOMe | C$_6$H$_5$— | 0 | |
| 42 | Cl | CN | p-Cl—C$_6$H$_4$— | 0 | |
| 43 | CHCl$_2$ | COOEt | p-Cl—C$_6$H$_4$— | 0 | 132–134 |
| 44 | OH | COOH | p-Cl—C$_6$H$_4$— | 0 | |
| 45 | C$_6$H$_5$— | COOEt | p-Cl—C$_6$H$_4$— | 0 | 160–161 |
| 46 | CH$_2$OCOCH$_3$ | COOEt | p-Cl—C$_6$H$_4$— | 0 | |
| 47 | NH$_2$ | COOH | p-Cl—C$_6$H$_4$— | 0 | |
| 48 | COO—n-Bu | COO—n-Bu | p-Cl—C$_6$H$_4$— | 0 | 66 |
| 49 | Me | COO—Sec-Bu | p-Cl—C$_6$H$_4$— | 0 | |
| 50 | Me | COOEt | p-OH—C$_6$H$_4$— | 0 | 215 |
| 51 | CF$_3$ | COOEt | p-Cl—C$_6$H$_4$— | 0 | 84–85 |
| 52 | OH | CN | p-Cl—C$_6$H$_4$— | 0 | >270 |
| 53 | Me | COOEt | p-CN—C$_6$H$_4$— | 0 | 136–137 |
| 54 | Me | COOEt | p-Cl—C$_6$H$_4$— | 1 | 130 |
| 55 | Me | COOEt | p-Br—C$_6$H$_4$— | 1 | 126–127 |
| 56 | Me | COOEt | p-NO$_2$—C$_6$H$_4$— | 1 | 210 |
| 57 | Me | COOEt | C$_6$H$_5$— | 1 | 119 |
| 58 | Me | COOEt | p-Me—C$_6$H$_4$— | 1 | 94 |
| 59 | Me | COOEt | p-F—C$_6$H$_4$— | 1 | 118 |
| 60 | Me | COOEt | p-MeO—C$_6$H$_4$— | 1 | 76 |
| 61 | Me | COOEt | o-Cl—C$_6$H$_4$— | 1 | 144 |
| 62 | Me | COOEt | 2,4-diCl—C$_6$H$_3$— | 1 | |
| 63 | Me | COOH | p-Cl—C$_6$H$_4$— | 1 | 278 (dec) |
| 64 | Me | CONH$_2$ | p-Cl—C$_6$H$_4$— | 1 | 286 (dec) |
| 65 | Me | CONHSO$_2$Me | p-Cl—C$_6$H$_4$— | 1 | |
| 66 | Me | COO—n-Bu | p-Cl—C$_6$H$_4$— | 1 | 93 |
| 67 | Me | CN | p-Cl—C$_6$H$_4$— | 1 | |

*dec = with decomposition

The compounds of general formula (I) wherein n is 0 can be prepared by reacting a compound of general formula (II)

$$\begin{array}{c} R^3-CH=CH-X \\ | \\ CHO \end{array}$$

wherein R$^3$ is as defined above and X is halogen (for example, chlorine or bromine) with a compound of general formula (III)

$$\begin{array}{c} H_2N-C=CH-R^2 \\ | \\ R^1 \end{array}$$

wherein R$^1$ and R$^2$ are as defined above, or a salt thereof. The reaction can be performed in known manner in an inert solvent for example dimethylformamide, cyclohexane, hexane, xylene or toluene. Preferably the reaction is performed at atmospheric pressure and at the reflux temperature of the solvent with removal of water formed in the reaction. The reaction is suitably performed over 4 to 20 hours.

The compounds of general formula (II) and (III) are known compounds and can be prepared in known manner. For example, the compound of general formula (II) can be prepared by reacting a compound of general formula (III)

$$R^3-CH_2-COOH$$

or a salt thereof, with a dialkylformamide (e.g. dimethylformamide) under the conditions of the Vilsmeir Reaction (e.g. using phosphorus oxychloride) to give a compound of general formula (IV)

$$R_3-C\begin{array}{c} CHN(R)_2 \\ \diagdown \\ CHO \end{array}$$

wherein R$_3$ is as defined above and each of the groups R, which may be the same or different, is alkyl for example $C_{1-4}$ alkyl preferably methyl or ethyl, which is converted in known manner (for example by reaction with phosgene) to the compound of general formula (II).

The compounds of general formula (I) wherein n is 1 can be prepared by oxidising a compound of general formula (I) wherein n is 0, or a salt thereof. The oxidation can be performed in known manner using, as oxidising agent, a persulphate, peroxide, peracid or perester; a preferred oxidising agent is acidic hydrogen peroxide, for example hydrogen peroxide in glacial acetic acid. Suitably the oxidation is performed at 0° to 60° C. for 2 to 24 hours in the presence of a suitable solvent, for example a polar solvent such as acetic acid.

The compounds of general formula (I) wherein $R^2$ is carboxy can be converted in known manner to the compounds of general formula (I) wherein $R^2$ is other than carboxy. For example, the compounds wherein $R^2$ is $COOR^5$ (i.e. esters) or is a group of general formula $—CONR^7R^8$ (i.e. amides) can be prepared by standard techniques [if necessary or desired via the acid halide (e.g. chloride)]. The compounds wherein $R^2$ is carboxy can be made by hydrolysis of the compounds wherein $R^2$ is $COOR^5$ while the compounds wherein $R^2$ is cyano can be prepared from the corresponding amides.

The compounds of general formula (I) wherein n is 1 are novel compounds and as such form part of the present invention. Some of the compounds of general formula (I) wherein n is 0 are also novel compounds; the present invention therefore also provides a compound of general formula (I) wherein $R^1$ is as defined above other than halogen or amino, M, $R^2$ and n are as defined above, and $R^3$ is halo-, haloalkyl- (e.g. trifluoromethyl-), haloalkoxy- (e.g. trifluoromethoxy-), nitro-, cyano-, hydroxy-, amino-, acylamino- (e.g. acetamido-), mono- or di-alkylamino-, $C_{1-4}$ alkyl-, $C_{1-4}$ alkoxy-, $C_{1-4}$ alkylthio-, $C_{1-4}$ alkylsulphinyl-, $C_{1-4}$ alkylsulphonyl-, $C_{2-6}$ alkenyl-, carboxy-, $C_{1-4}$ alkoxycarbonyl- or carboxamido-substituted phenyl, or when n is 0, an acid addition salt thereof.

As indicated above, the compounds of general formula (I) induce tillering in monocotyledonous plants, for example cereal plants (e.g. a wheat, barley, oats, rye, triticale, rice, sorghum or millet cultivar), forage and amenity grasses and sugar cane.

To induce tiller formation, the compounds are preferably applied in the form of compositions. The invention therefore also provides an agricultural composition comprising a novel compound of general formula (I) and a diluent or carrier.

The compounds may be applied for uptake by the plant either by bringing them directly into contact with plant foliage (e.g. by spraying) or by introducing them into the soil in which the roots of the plant grow, e.g. as a dressing on seeds.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. Microcapsules may be made by coacervation, or, more preferably, by stirred interfacial polymerisation of an isocyanate/diamine system. The microcapsules may be used as an aqueous suspension.

By including suitable additives, for example additives for improving the distribution, and adhesive power, the compositions can be better adapted for various utilities.

The compositions may also be in the form of liquid preparations for use as dips or sprays which are generally aqueous dispersions or emulsions containing the active ingredient in the presence of one or more surfactants e.g. wetting agents(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and the vegetable gums (for example, gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient(s). After dilution to form aqueous preparations, such preparations may contain varying amounts of the active ingredient(s) depending upon the intended purpose, but an aqueous preparation containing 0.01% to 10%, preferably 0.01% to 1%, by weight of active ingredient(s) may be used.

The compositions of this invention can comprise also other compound(s) having biological activity, e.g. compounds having similar of complementary plant growth regulating activity or compounds having fungicidal, selective herbicidal or insecticidal activity.

The fungicidal compound can be for example imazalil, benomyl, carbendazim, thiophanate-methyl, captafol, captan, sulphur, triforine, dodemorph, tridemorph ptrazophos, furalaxyl, ethirimol, tecnazene, dimethirimol, bupirimate, chlorothalonil, vinclozolin, procymidone, iprodione, metalaxyl, forsetyl-aluminium, carboxin, oxycarboxin, fenarimol, nuarimol, fenfurmam, methfuroxan, nitrotal-isopropyl, triadimefon, thiabendazole, etridiazole, triadimenol, biloxazol, dithianon, binapacryl, quinomethionate, guazitine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethylurea, fenapanil, ofurace, propiconazole, etaconazole and fenpropemorph.

Suitable insecticides are Pirimor, Croneton, dimethoate, Metasystox and formothion.

The other plant growth regulating compound can be one which is itself a tillering agent, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will be herbicides. Examples of suitable agents are the gibberellins (e.g GA$_3$, GA$_4$ or GA$_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzoaminopurine), phenoxyacetic acids (e.g. 2,4-D or MCPA), pyridyloxyphenoxypropionic acids, morphactins (e.g. chlorfluorecol), maleic hydrazide, glyphosine, dikegulac, fluoridamid, mefluidide, substituted quaternary ammonium and phosphonium compounds (e.g. chlormequat, mepiquat chloride or chlorphonium), ethephon, carbetamide, methyl-3, 6-dichloroanisate, asulam, abscissic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzopropmethyl and 3,6-dichloropicolinic acid.

The cereal tillers induced by the method of the invention can give rise to ripe grain-bearing ears at harvest ripe maturity. In grass swards, especially amenity grass, an increase in tillering can lead to a denser sward which may result in increased resilience to wear; in forage grass, it can lead to increased yields and better quality (e.g. improved digestibility and palatability). In sugar cane, increased tillering can lead to increased sugar yield.

The rate at which the compounds are applied in the field to induce tillering will depend on such factors as the particular cultivar to be treated, the particular compound to be applied, the growth stage of the plant at which the compound is to be applied and the climatic conditions prevailing at the time. However, suitable rates can be 50 g to 10 kg/ha, preferably 0.5 to 5 kg/ha. The growth stage at which the compound is applied can be any time prior to ear emergence on the main short axis. For temperate cereals, it is preferably during the early stages of tiller formation (in wheat and barley, this is at Feekes Scale 1 to 4 e.g. 2 to 4); alternatively the compound can be applied as a seed dressing.

The best growth stage and method of application for rice depends on how the rice is being grown.

In direct seeded rice, the compound may be sprayed or applied as granules to the irrigation water or to soil at any time after the second leaf has emerged. Applications may be throughout the tillering phase until the point where vegetative growth ceases and reproductive growth commences.

In transplanted rice, application may be made in any of the various ways described above from the time of transplanting to the end of tillering.

The compounds can be used to induce tillering in young rice seedling plants grown in nursery boxes or nurseries in preparation for transplanting out into the field. Therefore application may be made as a seed dressing, or as granules to the soil or irrigation water used in the nursery or as a foliar application to the plants.

In the treatment of rice plants, or rice crops the compounds can be applied for example as seed dressings or as granules, for example as slow release granules, to nursery boxes, paddy water etc.

The invention is illustrated by the following Examples.

EXAMPLE 1

5-(p-Chlorophenyl)-2-methyl-3-ethoxycarbonylpyridine (Compound 1)

Stage 1

Phosphorus oxychloride (28 ml) was added dropwise with stirring to dry dimethylformamide (38 ml) with cooling in an ice-bath to keep the temperature below 20° C. p-Chlorophenylacetic acid (17.05 g) was added, and the solution was heated to 70° C. for 6 hours and then left to stand overnight. The red solution was poured onto ice and neutralised with 40% sodium hydroxide whilst cooling in an ice/salt bath. Potassium carbonate (150 g) was added and the mixture was heated to boiling for 0.5 hour. The precipitate which formed was filtered off, washed well with water and recrystallised from carbon tetrachloride to give, as white crystals, 2-(p-chlorophenyl)-3-dimethylaminoprop-2-enal, m.p. 120° C.

Using the same technique, the following analogues of this compound can be prepared.

2-(p-bromophenyl)-3-dimethylaminoprop-2-enal m.p. 129°

2-(p-fluorophenyl)-3-dimethylaminoprop-2-enal m.p. 87°

2-(o-chlorophenyl)-3-dimethylaminoprop-2-enal m.p. 85°-66°

2-(p-trifluoromethylphenyl)-3-dimethylaminoprop-2-enal m.p. 90°–1°
2-(m-trifluoromethylphenyl)-3-dimethylaminoprop-2-enal m.p. 126°–7°
2-phenyl-3-dimethylaminoprop-2-enal liquid
2-(p-methylphenyl)-3-dimethylaminoprop-2-enal m.p. 132°–5°
2-(p-methoxyphenyl)-3-dimethylaminoprop-2-enal m.p. 88°–9°
2-(p-nitrophenyl)-3-dimethylaminoprop-2-enal m.p. 117°

Stage 2

The product (20.95 g) of Stage 1 was dissolved in alcohol-free chloroform (180 ml) and phosgene gas was bubbled through the stirred solution for 4 hours. The solution was evaporated down in vacuo to give a brown oil which was mixed with water. The emulsion so produced was twice extracted with diethyl ether, washed twice with water, dried (MgSO₄) and evaporated down in vacuo to give a light brown oil. The oil crystallised on standing to give 3-chloro-2-(p-chlorophenyl)prop-2-enal, m.p. 38°, which was used at once in the next stage.

Stage 3

The product (20.1 g) of Stage 2 and ethyl 3-aminocrotonate (27.1 g) were refluxed in cyclohexane (200 ml) using a Dean and Stark apparatus to separate off the water produced in the reaction. After 10 hours, the suspension was cooled and filtered to remove the insoluble material and the filtrate was then evaporated down in vacuo. The red oil produced was shaken with diethyl ether (50 ml) and 4M-hydrochloric acid (100 ml) added to give a copious precipitate of the pyridine hydrochloride which was filtered off and washed well with diethyl ether. The pink solid was dissolved in diethyl ether and 2M-sodium hydroxide. The etheral solution was separated off, washed thrice with water, dried (MgSO₄) and evaporated down in vacuo to give a pink solid which was recrystallised from aqueous ethanol to give, as white crystals, 5-(p-chlorophenyl)-2-methyl-3-ethoxycarbonylpyridine, m.p. 71°.

EXAMPLE 2

5-(p-Chlorophenyl)-2-methyl-3-pyridine carboxylic acid (Compound 10)

5-(p-Chlorophenyl)-2-methyl-3-ethoxycarbonylpyridine (25 g) was suspended in sodium hydroxide (3.99 g) in ethanol (100 ml) and water (50 ml). Stirring at room temperature for 3 hours gave a solution which was concentrated to dryness. The residue was dissolved in water and the solution washed with ethyl acetate; its pH was then brought to 5. The product which precipitated was collected, washed well with water and then with acetone and then dried to give the title compound (20.94 g), m.p. 297°–300° (dec).

EXAMPLE 3

5-(p-Chlorophenyl)-2-methyl-3-n-propoxycarbonyl-pyridine (Compound 16)

5-(p-Chlorophenyl)-2-methyl-3-pyridine carboxylic acid (2 gm) and p-toluenesulphonic acid (1.69 g) in n-propanol (125 ml) was refluxed for 15 hours. The solution was concentrated and the residue partitioned between methylene dichloride and aqueous sodium carbonate. The organic phase was separated, washed with water, dried and concentrated to an oil which slowly crystallised to give the title compound (0.66 g), m.p. 54°–7°.

EXAMPLE 4

5-(p-Chlorophenyl)-2-methyl-3-tert-butoxycarbonyl-pyridine (Compound 17)

Stage 1

Oxalyl chloride (11.52 gms) in dry methylene dichloride (10 ml) was slowly added to a suspension of 5-(p-chlorophenyl)-2-methyl-3-pyridine carboxylic acid (10 g) in dry methylene dichloride (50 ml). After standing for 1 hour at room temperature, the mixture was concentrated and the residue washed with dry diethyl ether, collected and dried to give 5-(p-chlorophenyl)-2-methyl-3-chlorocarbonylpyridine hydrochloride (11.95 g).

Stage 2

Tert-butanol (1.08 g) and dry pyridine (1.31 g) in dry methylene dichloride (20 ml) were added dropwise to the product (2 g) of Stage 1 in dry methylene dichloride (40 ml). After stirring at room temperature for 2 hours, potassium tert-butoxide (1 g) was added and stirring was continued for a further hour. The mixture was washed twice with water, dried and filtered through a bed of activated charcoal and silica. Concentration of the filtrate gave the title product (0.42 g), m.p. 70°–72°.

EXAMPLE 5

5-(p-Chlorophenyl)-2-methyl-3-N-(methanesulphonyl) carboxamidopyridine (Compound 12)

5-(p-Chlorophenyl)-2-methyl-3-chlorocarbonylpyridine hydrochloride (3 g) in dry pyridine (20 ml) was added dropwise to methane sulphonamide (1.98 g) in dry pyridine (30 ml). The solution was stirred overnight at room temperature and then refluxed for 2 hours. The mixture was cooled and concentrated. Water was added to the residue and the mixture made alkaline with triethylamine and then washed with ethyl acetate. The pH of the aqueous phase was brought to 5 with acetic acid and the mixture extracted with ethyl acetate. The extract was washed with water, dried and concentrated to a solid which was dissolved in acetone. The mixture was filtered and the filtrate concentrated to give the crude product which was recrystallised from acetone-petroleum ether (b.p. 30°–40°), washed with diethyl ether and dried to give the title compound (1.71 g), m.p. 209°–11°.

EXAMPLE 6

5-(p-Chlorophenyl-2-methyl-3-(N-phenylcarboxamido) pyridine (Compound 24)

A suspension of 5-(p-chlorophenyl)-2-methyl-3-pyridine carboxylic acid (2.00 g) in dry tetrahydrofuran (200 ml) containing N,N'-carbonyldiimadazole (1.32 g) was stirred for 1.5 hours. Aniline (1.50 g) was then added and the solution stood at room temperature overnight prior to concentration. The residue was partitioned between water and methylene dichloride. The organic phase was separated, washed with sodium carbonate solution and water, dried and the residue concentrated to a solid which was washed with diethyl ether and dried to give the title compound (2.05 g), m.p. 79°–82°.

EXAMPLE 7

5-(p-Chlorophenyl)-3-cyano-2-methylpyridine (Compound 14)

5-(p-Chlorophenyl)-2-methyl-3-carboxamidopyridine (1.50 g) was added portionwise to phosphorus oxychloride (25 ml). The mixture was heated at 100° C. for 2 hours. The resulting solution was concentrated and the residue suspended in water. The pH of the mixture was brought to 11 with ammonia solution and the mixture was extracted with diethyl ether. The extract was washed with water, dried and filtered through charcoal and silica. The filtrate was concentrated, and the residue was washed with petroleum ether (b.p. 30°–40°), collected and dried to give the title compound (1.27 g), m.p. 158°–9°.

EXAMPLE 8

5-(p-Aminophenyl)-3-ethoxycarbonyl-2-methylpyridine (Compound 34)

3-Ethoxycarbonyl-2-methyl-5-(p-nitrophenyl)pyridine (2 g) was dissolved in warm ethanol (70 ml). Iron powder (4 g) was added to the solution followed by water (7 ml) containing 2 drops of 11.5 N-hydrochloric acid. The mixture was refluxed for 1.5 hours, cooled and filtered. The filtrate was concentrated and the residue dissolved in methylene dichloride. The solution was washed with water, dried and concentrated. The crude product was recrystallised from methylene dichloride-petroleum ether (b.p. 30°–40°) to give the title compound (1.23 g), m.p. 137°–8°.

EXAMPLE 9

5-(4-Amino-3,5-dibromophenyl)-3-ethoxycarbonyl-2-methylpyridine (Compound 37)

Bromine (0.43 ml) in dry methylene dichloride (10 ml) was added dropwise to 5-(4-aminophenyl)-3-ethoxycarbonyl-2-methylpyridine (1 gm) in dry methylene dichloride (20 ml). The mixture was stirred for 2 hours and then triethylamine (2.0 ml) was added. After a further 0.5 hour stirring, the mixture was diluted with more solvent and washed with sodium bicarbonate solution and water, dried and concentrated. The crude product was recrystallised from methylene dichloride-petroleum ether (b.p. 30°–40°) to give the title compound (1.26 g), m.p. 171° (dec).

EXAMPLE 10

5-(3,5-Dibromophenyl)-3-ethoxycarbonyl-2-methylpyridine (Compound 33)

Hydrochloric acid (11.5N, 0.90 ml) was added to 5-(4-amino-3,5-dibromophenyl)-3-ethoxycarbonyl-2-methyl pyridine (2 g) in glacial acetic acid (20 ml). Sodium nitrite (0.37 g) in water (2 ml) was added at 0°–5° C. and, after standing for 0.5 hour at this temperature, the mixture was poured into 30% aqueous hypophosphorous acid (3.88 g) in water (10 ml). The mixture was stirred at room temperature for 0.5 hour, diluted with water, made alkaline with triethylamine and extracted with diethyl ether. The extract was washed with sodium bicarbonate solution and water, dried and filtered through a column of silica. Concentration of the filtrate and recrystallisation of the residue from petroleum ether (b.p. 40°–60°) gave the title compound (0.97 g), m.p. 100°–2°.

EXAMPLE 11

5-(p-Chlorophenyl)-2-dichloromethyl-3-ethoxycarbonyl pyridine (Compound 43)

5-(p-Chlorophenyl)-3-ethoxycarbonyl-2-methylpyridine (1.38 g) in glacial acetic acid (15 ml) containing acetic anhydride (5 drops) was treated with anhydrous sodium acetate (1.40 g) and the mixture was warmed to 50° C. Chlorine gas was passed into the mixture for 4.5 hours. The mixture was left overnight at room temperature and then poured into iced water. The resulting mixture was extracted with methylene dichloride. The extract was washed with water and sodium bicarbonate solution, dried and concentrated. The residue was triturated with petroleum ether (b.p. 40°–60°) and the crude product was filtered. The residue was recrystallised from petroleum ether (b.p. 60°–80°) to give the title product (0.62 g), m.p. 132°–4°.

EXAMPLE 12

5-(p-Chlorophenyl)-3-ethoxycarbonyl-2-trifluoromethylpyridine (Compound 51)

Ethyl 3-amino-4,4,4-trifluorocrotonate (1.55 g; prepared by the method of Swarts, Bull. Sci. acad. roy. Belg., 1926, 12 (5), 679) in dry dimethylformamide (2 ml) was added dropwise to a suspension of sodium hydride (0.20 g) in dimethylformamide (20 ml). The mixture was then stirred for 30 minutes and 3-chloro-2-(p-chlorophenyl)prop-2-enal (1.7 g) was added dropwise. The mixture was stirred for 2 hours, allowed to stand overnight and poured into water. The resulting mixture was twice extracted with diethyl ether and the combined extracts washed with water, dried and filtered through charcoal. The filtrate was concentrated and the residue recrystallised from aqueous ethanol to give the title compound (1.1 g), m.p. 84°–5°.

EXAMPLE 13

5-(p-Chlorophenyl)-2-methyl-3-ethoxycarbonylpyridine N-oxide (Compound 54)

Hydrogen peroxide (100 vol.; 65.6 ml) was added to glacial acetic acid (250 ml) with stirring and the solution was heated to 50°. 5-(p-Chlorophenyl-2-methyl-3-ethoxycarbonylpyridine (27.55 g) was added and the solution stirred at 50°–55° for 16 hours. The volume of the solution was halved by evaporation in vacuo at below 50° C., and the mixture was then poured into water and neutralised with 2M-sodium hydroxide. The precipitate so formed was filtered off and washed with water to give a white solid which was recrystallied from carbon tetrachloride to give, as white crystals, the title compound, m.p. 130°.

EXAMPLE 14

The tiller inducing activity of the compounds was determined as follows.

Spring wheat (variety Sappo) and spring barley (variety Sundance) were grown three per 8 cm diameter pot in John Innes Potting Compost No 2. When the plants had developed to the 2 leaf (fully expanded) stage, i.e. before tiller emergence, they were treated with a foliar spray of the test compound at a rate of 0.3, 1 and 3 kg per hectare and applied at a volume equivalent to 1000 liters per hectare. Four replicate pots per treatment were used. The test compound was formulated by suspending 5 g of it in 100 ml of a formulation of cyclohexanone (95% by weight), Synperonic NPE 1800 (3.3% by weight) and Tween 85 (1.7%). The plants were assessed 27 days after treatment. At assessment, the number of tillers was recorded and compared with the results for plants treated with the formulation alone to give the controls. The results for the test compound are shown in Table II as a percentage of the control value.

TABLE II

| Compound | Rate (kg/ha) | Wheat Tiller Number Expressed as Percentage of Control | Barley Tiller Number Expressed as Percentage of Control |
|---|---|---|---|
| 1 | 0.3 | 104 | 132 |
|   | 1.0 | 144 | 136 |
|   | 3.0 | 140 | 136 |
| 6 | 0.3 | 84 | 121 |
|   | 1.0 | 84 | 113 |
|   | 3.0 | 104 | 105 |
| 5 | 0.3 | 80 | 87 |
|   | 1.0 | 72 | 79 |
|   | 3.0 | 80 | 72 |
| 3 | 0.3 | 80 | 98 |
|   | 1.0 | 108 | 79 |
|   | 3.0 | 104 | 98 |
| 2 | 0.3 | 140 | 109 |
|   | 1.0 | 160 | 124 |
|   | 3.0 | 216 | 155 |
| 8 | 0.3 | 108 | 75 |
|   | 1.0 | 88 | 98 |
|   | 3.0 | 92 | 109 |
| 11 | 0.3 | 84 | 102 |
|   | 1.0 | 80 | 106 |
|   | 3.0 | 80 | 102 |

EXAMPLE 15

The tiller inducing activity of the compounds was also determined as follows.

Spring wheat (variety Sappo) and spring barley (variety Julia) were grown four per 10 cm diameter pot in sphagnum peat compost. When the plants had developed to the 1.5 to 2 leaf (fully expanded) stage, i.e. before tiller emergence, they were treated with a foliar spray of the test compound at a rate of 2 and 4 kilograms per hectare and applied at a volume equivalent to 1000 liters per hectare. For each rate, 20 pots were planted. The test compound was formulated by suspending 5 g of it in 100 ml of a formulation of cyclohexanone (95% by weight), Synperonic NPE 1800 (3.3% by weight) and Tween 85 (1.7%). The plants were assessed 7, 14, 21 and 28 days after treatment (DAT). At each assessment, the plants in 5 pots were harvested. The number of tillers was recorded and compared with the results for plants treated with the formulations alone to give the controls. The results are shown in Table III.

TABLE III

| Compound | Rate (kg/ha) | DAT | Tiller Number per plant (Sappo) | Tiller Number per plant (Julia) |
|---|---|---|---|---|
| 54 | 2 | 7 | 1.4 | 1.9 |
| 54 | 4 | 7 | 1.5 | 2.0 |
| Control | — | 7 | 0.6 | 1.3 |
| 54 | 2 | 14 | 3.3 | 3.6 |
| 54 | 4 | 14 | 3.4 | 3.5 |
| Control | — | 14 | 2.2 | 2.2 |
| 54 | 2 | 21 | 3.3 | 3.0 |
| 54 | 4 | 21 | 3.3 | 3.2 |
| Control | — | 21 | 2.2 | 2.9 |
| 54 | 2 | 28 | 3.2 | 3.4 |
| 54 | 4 | 28 | 3.3 | 3.9 |

TABLE III-continued

| Compound | Rate (kg/ha) | DAT | Tiller Number per plant (Sappo) | Tiller Number per plant (Julia) |
|---|---|---|---|---|
| Control | — | 28 | 2.1 | 2.8 |

EXAMPLE 16

This Example further illustrates the tillering activity of the compounds on wheat and barley. Compounds were applied as an emulsifiable concentrate diluted to give a concentration of 4000 ppm and applied as an overall spray using a track sprayer. This concentration was equivalent to a rate of 4.0 kg/ha. Plants were grown in 7 cm pots containing a peat based compost and sprayed at the 2 leaf stage. Tillering (and phytotoxic effects) were assessed 19 days after application of the compound. Tillering was scored on a 0–3 scale in each pot where:
   0 = no increase in tillers
   1 = an increase of 0.5–1.0 tillers per plant
   2 = an increase of 1.0–1.5 tillers per plant
   3 = an increase of 1.5 or greater
Duplicate pots of barley and wheat were used giving a maximum aggregate score on each species of 6 out of 6. Phytotoxicity was also assessed on an individual pot basis on a 0–5 scale giving a maximum aggregate score on each species of 10 out of 10.

The results are shown in Table IV below.

TABLE IV

| COMPOUND NO | WHEAT TILLERING (0–6) | WHEAT PHYTOTOXICITY (0–10) | BARLEY TILLERING (0–6) | BARLEY PHYTOTOXICITY (0–10) |
|---|---|---|---|---|
| 54 | 2 | 0 | 3 | 0 |
| 55 | 5 | 0 | 2 | 0 |
| 56 | 0 | 0 | 3 | 0 |
| 57 | 0 | 1 | 0 | 0 |
| 58 | 0 | 0 | 2 | 0 |
| 59 | 0 | 0 | 1 | 0 |
| 60 | 0 | 0 | 3 | 0 |
| 61 | 0 | 0 | 0 | 0 |
| 66 | 5 | 0 | 0 | 0 |
| 64 | 0 | 0 | 0 | 2 |
| 2 | 6 | 0 | 4 | 0 |
| 3 | 0 | 1 | 2 | 0 |
| 4 | 0 | 0 | 0 | 0 |
| 7 | 0 | 2 | 0 | 3 |
| 5 | 0 | 0 | 2 | 0 |
| 6 | 2 | 0 | 3 | 1 |
| 8 | 0 | 0 | 2 | 0 |
| 48 | 2 | 0 | 1 | 0 |
| 10 | 2 | 0 | 0 | 0 |
| 15 | 1 | 0 | 2 | 0 |
| 1 | 5 | 1 | 5 | 0 |
| 16 | 3 | 0 | 4 | 0 |
| 13 | 1 | 0 | 2 | 0 |
| 17 | 1 | 0 | 2 | 0 |
| 18 | 3 | 2 | 2 | 3 |
| 19 | 1 | 0 | 3 | 0 |
| 20 | 2 | 0 | 1 | 0 |
| 21 | 0 | 0 | 0 | 0 |
| 11 | 3 | 0 | 1 | 1 |
| 22 | 0 | 0 | 0 | 0 |
| 23 | 0 | 0 | 0 | 0 |
| 24 | 0 | 0 | 2 | 0 |
| 12 | 1 | 0 | 1 | 0 |
| 25 | 1 | 0 | 0 | 0 |
| 14 | 3 | 0 | 0 | 0 |
| 26 | 2 | 0 | 0 | 0 |
| 27 | 2 | 0 | 0 | 0 |
| 28 |   |   |   |   |
| 29 |   |   |   |   |
| 30 | 3 | 0 | 4 | 0 |

TABLE IV-continued

| COMPOUND NO | WHEAT | | BARLEY | |
|---|---|---|---|---|
| | TILLERING (0-6) | PHYTOTOXICITY (0-10) | TILLERING (0-6) | PHYTOTOXICITY (0-10) |
| 31 | 2 | 0 | 1 | 0 |
| 32 | 3 | 0 | 0 | 0 |
| 33 | 3 | 0 | 0 | 0 |
| 34 | 1 | 0 | 1 | 0 |
| 35 | 2 | 0 | 1 | 0 |
| 36 | | | | |
| 37 | 3 | 0 | 0 | 0 |
| 38 | 0 | 0 | 0 | 0 |
| 39 | 0 | 0 | 0 | 0 |
| 40 | 0 | 0 | 0 | 0 |
| 41 | 2 | 0 | 0 | 0 |
| 42 | 0 | 0 | 0 | 0 |
| 43 | | | | |
| 44 | 0 | 0 | 0 | 0 |
| 45 | | | | |
| 46 | 0 | 0 | 0 | 0 |
| 47 | 0 | 0 | 0 | 0 |

We claim:

1. A compound of general formula (I):

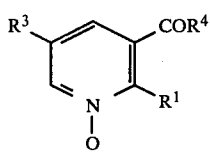

wherein $R^1$ is optionally halo- or acetoxy- substituted $C_{1-4}$ alkyl;

$R^4$ is —OH, —OM or —OR$^5$ wherein

M is a cation selected from an alkali metal, alkaline earth metal, copper or iron ion or a mono-, di-, tri- or tetra ($C_{1-6}$ alkyl) substituted or unsubstituted ammonium ion;

$R^5$ is $C_1$-$C_4$ alkyl, —CH$_2$CH=CH$_2$, hydroxyethyl, benzyl or phenyl; and $R^3$ is phenyl, o-, m- or p- fluoro-, chloro-, bromo-, cyano-, acetylamino-, amino-, nitro-, methyl-, trifluoromethyl- or methoxy-phenyl, 2,4-dichlorophenyl, 3,5-dibromophenyl, 3-bromo-4-aminophenyl or 3,5-dibromo-4-aminophenyl.

2. A compound as claimed in claim 1 wherein $R^1$ is methyl.

3. A compound as claimed in claim 1 wherein $R^2$ is ethoxy- or n-propoxy-carbonyl.

4. A compound as claimed in claim 1 which is 5-(p-chlorophenyl)-2-methyl-3-ethoxycarbonylpyridine N-oxide.

5. A method of inducing tiller formation in a monocotyledonous plant, said method consisting essentially of the step of applying to the plant, to seed to the plant or to the locus surrounding the plant or seed, a tiller formation inducing amount of a compound as claimed in claim 1.

6. A method as claimed in claim 5 wherein the plant is a cereal plant, a forage or amenity grass or sugar cane.

7. A method as claimed in claim 5 wherein the compound is as claimed in claim 4.

8. An agricultural composition consisting essentially of a tiller formation inducing amount of a compound of general formula (I) according to claim 1, and a diluent or carrier.

9. A composition as claimed in claim 8 wherein the compound is as claimed in claim 4.

* * * * *